(12) United States Patent
Carbonari et al.

(10) Patent No.: US 8,877,999 B2
(45) Date of Patent: Nov. 4, 2014

(54) DISPOSABLE ABSORBENT PRODUCT WITH SHAPED FLUID STORAGE STRUCTURES

(75) Inventors: Raquel Carbonari, Philadelphia, PA (US); Thomas Bergin, Conshohocken, PA (US); Jehann Biggs, Mount Vernon, NY (US); Lauren Entrekin, Upper Darby, PA (US); Frank Steven Glaug, Chester Springs, PA (US); Lizelle Canlas Valdecanas, Glen Mills, PA (US); Linda Morrell-Schwartz, Bensalem, PA (US); Jorge Sievert Nieri, Knoxville, TN (US); Ramon Andres Urteaga, Bala Cynwyd, PA (US)

(73) Assignee: SCA Hygiene Products AB, Gothenburg (SE)

( * ) Notice: Subject to any disclaimer, the term of this patent is extended or adjusted under 35 U.S.C. 154(b) by 259 days.

(21) Appl. No.: 13/553,278

(22) Filed: Jul. 19, 2012

(65) Prior Publication Data
US 2013/0090620 A1   Apr. 11, 2013

Related U.S. Application Data

(63) Continuation-in-part of application No. 13/269,292, filed on Oct. 7, 2011.

(51) Int. Cl.
*A61F 13/15*   (2006.01)
*A61F 13/494*   (2006.01)
(Continued)

(52) U.S. Cl.
CPC ............... *A61F 13/49466* (2013.01); *A61F 2013/530547* (2013.01); *A61F 2013/4581* (2013.01); *A61F 2013/530562* (2013.01); *A61F 13/47245* (2013.01); *A61F 13/47236* (2013.01); *A61F 13/49001* (2013.01); *A61F 13/4946* (2013.01); *A61F 13/535* (2013.01); *A61F 13/15658* (2013.01); *A61F 13/15699* (2013.01); *A61F 13/15707* (2013.01); *A61F 13/4704* (2013.01); *A61F 13/4755* (2013.01); *A61F 13/4756* (2013.01)
USPC .......................................................... 604/378

(58) Field of Classification Search
CPC ................... A61F 13/47236; A61F 13/47245; A61F 13/47254; A61F 2013/4568; A61F 2013/4581; A61F 2013/530547; A61F 2013/530562
USPC .......................................................... 604/378
See application file for complete search history.

(56) References Cited

U.S. PATENT DOCUMENTS 4,184,498 A   1/1980 Franco
5,429,629 A   7/1995 Latimer et al.
(Continued)

FOREIGN PATENT DOCUMENTS

EP   2130521 A1   12/2009
WO   02/085270   10/2002
(Continued)

*Primary Examiner* — Lynne Anderson
(74) *Attorney, Agent, or Firm* — Drinker Biddle & Reath LLP

(57) ABSTRACT

A disposable absorbent product includes a backsheet, a topsheet overlaying the backsheet, and a core disposed between the backsheet and topsheet for retaining fluid secreted by a wearer of the absorbent product. The core has a length dimension, a width dimension, and a thickness dimension orthogonal to the length and width dimensions. The core includes first and second fluid storage structures, with the first fluid storage structure at least partially surrounding the second fluid storage structure in the thickness dimension. The second fluid storage structure extends along a longitudinal axis and has a head portion, as well as a pair of leg portions, with the leg portions being longitudinally opposed the head portion. Each of the leg portions extends along a minor axis that defines, with the longitudinal axis, an acute included angle.

21 Claims, 7 Drawing Sheets

(51) Int. Cl.
*A61F 13/472* (2006.01)
*A61F 13/49* (2006.01)
*A61F 13/535* (2006.01)
*A61F 13/47* (2006.01)
*A61F 13/475* (2006.01)
*A61F 13/53* (2006.01)
*A61F 13/45* (2006.01)

(56) References Cited

U.S. PATENT DOCUMENTS 5,462,541 A * 10/1995 Bruemmer et al. ........... 604/391
5,514,104 A *  5/1996 Cole et al. .................... 604/366
5,792,130 A *  8/1998 Widlund et al. ......... 604/385.01
5,855,572 A     1/1999 Schmidt
D455,829  S     4/2002 Drevik et al.
6,740,069 B2    5/2004 Drevik
6,844,482 B2    1/2005 Eliasson
6,866,658 B2 *  3/2005 Drevik et al. ............ 604/385.31
8,366,696 B2 *  2/2013 Konawa ................... 604/385.01
2004/0087928 A1 5/2004 Ducker
2007/0197987 A1 8/2007 Tsang et al.

FOREIGN PATENT DOCUMENTS

WO    03/055431      7/2003
WO    2006/105305   10/2006

* cited by examiner

DISPOSABLE ABSORBENT PRODUCT WITH SHAPED FLUID STORAGE STRUCTURES

CROSS-REFERENCE TO RELATED APPLICATIONS

The present application is a continuation-in-part of pending U.S. patent application Ser. No. 13/269,292, entitled "DISPOSABLE ABSORBENT PRODUCT WITH MULTIPLE FLUID STORAGE STRUCTURES AND RELATED METHODS," filed 7 Oct. 2011, and the entire contents of which are hereby incorporated by reference herein.

TECHNICAL FIELD

The present invention is generally related to absorbent products and, more particularly, to disposable absorbent products worn by humans for the containment and absorption of fluid bodily secretions.

BACKGROUND

Disposable absorbent products for absorption of bodily fluids are available in different types, designs, and dimensions. For example, baby diapers, adult diapers, baby pants, adult pants, and incontinence guards, are products designed for the containment of urine and excrement. There are other types of disposable absorbent articles, such as feminine hygiene products (e.g., heavy and light incontinence pads, pantiliners) that are designed to contain and absorb urine and/or menses secreted by female wearers. Known products of this type typically include a topsheet facing the body of the wearer, a backsheet facing the garment worn by the wearer, and an absorbent core sandwiched between the topsheet and backsheet.

In conventional products of that type, the core may include a pair of discrete fluid storage structures, for example stacked over one another. U.S. Pat. No. 5,855,572 illustrates that type of design. This type of stacked arrangement, however, may result in products that are relatively bulky and therefore unappealing and/or uncomfortable to the wearer.

Other known products have addressed the above-discussed bulkiness by having a core in which one of the discrete fluid storage structures is a relatively thin layer of absorbent material, such as an airlaid-based structure or a foam structure. A problem with some of these thin layers of material is their rigidity, and more specifically the rigidity along the edges and at the corners of those layers, especially when cut with a die along the perimeter. The pressure of the die cutting through the material creates a compressed and densified edge, which is stiff and uncomfortable against the thighs of the wearer. And while rounded/chamfered corners and/or edges may address the problems associated with the rigidity of these materials, the required rounding/chamfering increases the overall cost and complexity of the manufacturing processes involved. Moreover, rounding/chamfering may result in the production of trimmed portions of material, which further increases material costs, and may require additional equipment and processes for recycling or disposition of those trimmed portions. Additionally, the rounding/chamfering of fluid storage structures of this type reduces the overall absorption capacity of the products of which those structures form part, by virtue of the removal of those portions of material otherwise available for storing fluid.

It would be advantageous, therefore, to provide disposable absorbent products, and related methods, that address these and other shortcomings of conventional disposable absorbent products of the type described above.

BRIEF DESCRIPTION OF THE DRAWINGS

The objectives and features of the invention will become more readily apparent from the following detailed description taken in conjunction with the accompanying drawings in which.

SUMMARY

Figure 1:
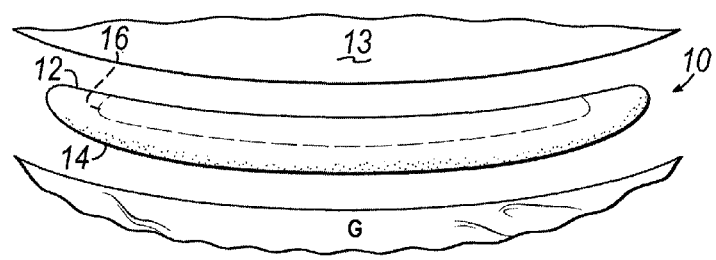
FIG. 1 is a perspective view of a disposable absorbent product in accordance with one embodiment of the invention.

In one embodiment, a disposable absorbent product is provided. The absorbent product includes a backsheet, a topsheet overlaying the backsheet, and a core disposed between the backsheet and topsheet for retaining fluid secreted by a wearer of the absorbent product. The core has a length dimension, a width dimension, and a thickness dimension orthogonal to the length and width dimensions. The core includes first and second fluid storage structures, with the first fluid storage structure at least partially surrounding the second fluid storage structure in the thickness dimension. The second fluid storage structure extends along a longitudinal axis and has a head portion, as well as a pair of leg portions, with the leg portions being longitudinally opposed the head portion. Each of the leg portions extends along a minor axis that defines, with the longitudinal axis, an acute included angle.

In another embodiment, a disposable absorbent product is provided that includes a backsheet, a topsheet overlaying the backsheet, and a core disposed between the backsheet and topsheet for retaining fluid secreted by a wearer of the disposable absorbent product. The core has a length dimension, a width dimension, and a thickness dimension orthogonal to the length and width dimensions. The core includes first and second fluid storage structures, with the first fluid storage structure at least partially surrounding the second fluid storage structure in the thickness dimension. The second fluid storage structure has a head portion and a pair of leg portions that are longitudinally opposed the head portion. Each of the leg portions extends along a minor axis defining an included angle of less than about 40° between them. Further, each of the leg portions has a length that is greater than about 20% of the overall length of the second fluid storage structure.

In another embodiment, a disposable absorbent product is provided that includes a backsheet, a topsheet overlaying the backsheet, and a core disposed between the backsheet and topsheet for retaining fluid secreted by a wearer of the disposable absorbent product. The core has a length dimension, a width dimension, and a thickness dimension orthogonal to the length and width dimensions. The core includes first and second fluid storage structures, with the first fluid storage structure at least partially surrounding the second fluid storage structure in the thickness dimension. The second fluid storage structure has a generally heart-shaped head portion and a pair of leg portions longitudinally opposed the head portion. Each of the leg portions has a length that is less than about 10% of the overall length of the second fluid storage structure. The second fluid storage structure includes an arcuate depression defining a juncture between the leg portions.

In yet another embodiment, an absorbent core is provided for use in an absorbent product. The absorbent core has a first fluid storage structure and a second fluid storage structure. The core has length dimension, a width dimension, and a thickness dimension orthogonal to the length and width dimensions. The first fluid storage structure at least partially surrounds the second fluid storage structure in the thickness dimension, and the second fluid storage structure extends along a longitudinal axis and includes a head portion and a pair of leg portions longitudinally opposed the head portion. Each of the leg portions extends along a minor axis defining an acute included angle with the longitudinal axis.

DETAILED DESCRIPTION

To the extent that any meaning or definition of a term in this written document conflicts with any meaning or definition of the term in a document incorporated by reference, the meaning or definition assigned to the term in this written document shall govern. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

With reference to the figures, and more particularly to FIG. 1, an exemplary disposable absorbent product in the form of a feminine pad 10 includes a topsheet 12, and a backsheet 14 disposed opposite the topsheet 12. When worn, the topsheet 12 faces the body of the wearer, schematically represented and assigned the numeral 13, while the backsheet 14 faces away from the body 13 of the wearer. In the case of known uses of feminine pads and similar products, the backsheet 14 faces a garment G worn by the wearer. While not shown, the feminine pad 10 may include one or more features such as lateral extensions resembling wings, adhesive components, or mechanical entanglement-type (hook-and-loop) fasteners that allow the wearer to secure the pad 10 to the garment G. Additionally or alternatively, and while also not shown, the pad 10 may include adhesive or mechanical components that allow the pad 10 to be secured directly onto the body 13 of the wearer. The pad 10 also includes a core, generally assigned the numeral 16, that is configured to absorb and retain body fluids, such as urine and/or menses, secreted by the wearer.

Figure 2:
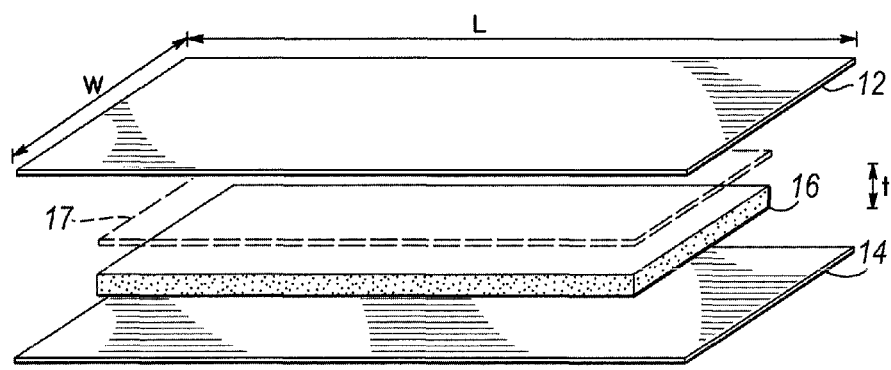
FIG. 2 is a partially disassembled view of the disposable absorbent product of FIG. 1.
Figure 3:
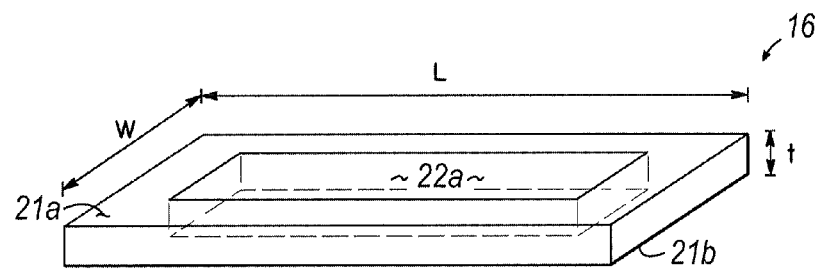
FIG. 3 is a perspective view of a core of the disposable absorbent product of FIGS. 1 and 2.
Figure 4:
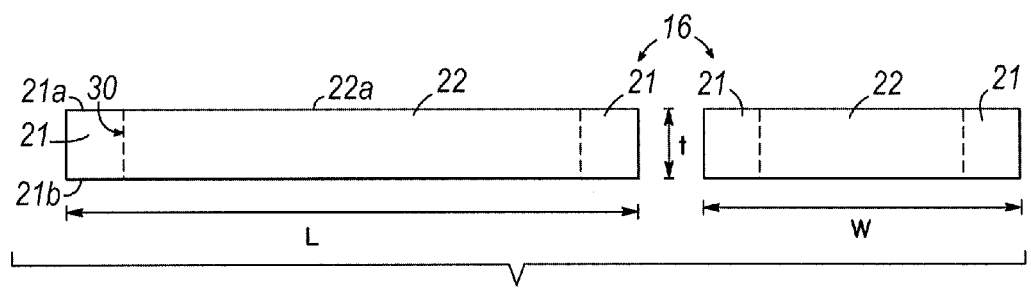
FIG. 4 shows lateral and frontal elevation views of the core of FIG. 3.

With continued reference to FIG. 1, and further referring to FIGS. 2-4, the core 16 and the pad 10 of which core 16 forms part, extend along a length dimension L, a width dimension W, and a thickness dimension t orthogonal to the length and width dimensions L, W. Further, the core 16 has a generally rectangular outer profile in the plane defined by the length and width dimensions L, W (the "product plane"), although those of ordinary skill in the art will readily appreciate that such shape is exemplary rather than limiting. For example, and without limitation, the core 16 may instead have a generally hourglass shape, or some other regular or irregular shape, symmetrical or asymmetrical. The core 16 may optionally include an acquisition layer 17 (FIG. 2) or similar structure that is primarily designed to acquire and/or distribute fluids received through the topsheet 12 and direct same toward other portions of the core 16 that are primarily designed to store the fluid, as explained in further detailed below. In that regard, it is contemplated that the optional acquisition layer 17 may, in certain embodiments, be free of fluid-storage materials such as superabsorbent material ("SAP") and/or be free of fluff pulp.

Referring particularly to FIGS. 3 and 4, the core 16 of that exemplary embodiment includes two discrete fluid storage structures, although the principles disclosed herein are similarly applicable to cores having more than two discrete fluid storage structures. In the illustrative embodiment of FIGS. 3 and 4, a first fluid storage structure 21 and a second fluid storage structure 22 are arranged in the core 16 such that the first fluid storage structure 21 surrounds the second fluid storage structure 22 in the thickness dimension t, as illustrated in those figures. More specifically in that embodiment, the second fluid storage structure 22 rests within a centrally located hole or opening 30 that extends through the entire thickness of the first fluid storage structure 21 i.e., between the top and bottom surfaces 21a, 21b of the first fluid storage structure 21. While not shown, the core 16 may also include other components such as non-woven or paper-based materials (e.g., tissue) that at least partially wrap the first and second fluid storage structures 21, 22.

Figure 5:
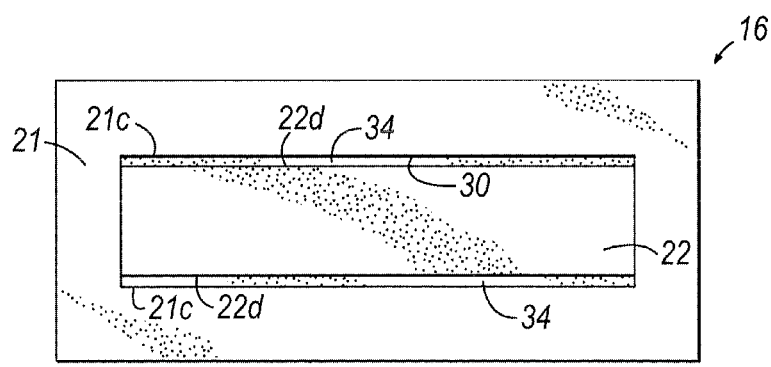
FIG. 5 is a top view of the core of FIGS. 3 and 4.
Figure 6:
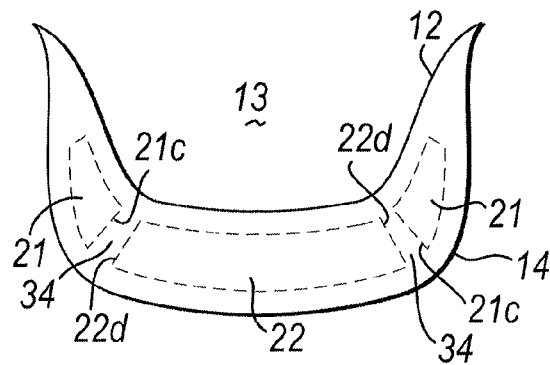
FIG. 6 is a frontal elevation view of the core of FIGS. 3-5 during use.
Figure 7:
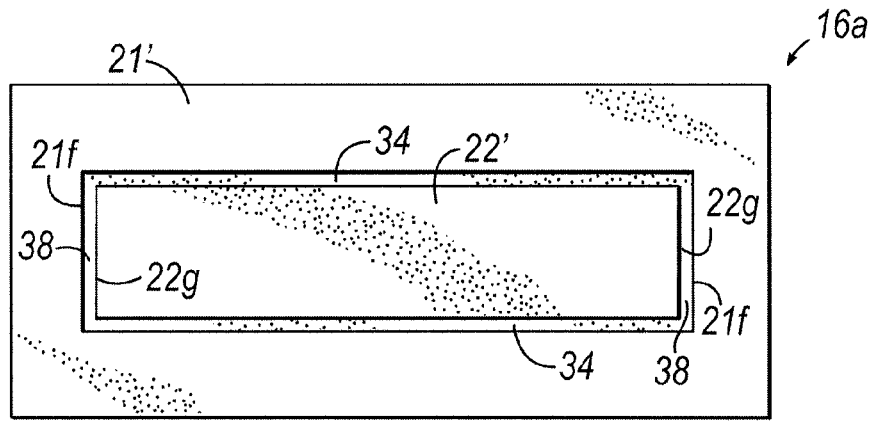
FIG. 7 is a top view, similar to FIG. 5, illustrating a core in accordance with another embodiment of the invention.

Referring further now to FIGS. 5-8, the size and shape of the first and second fluid storage structures 21, 22 may be chosen such that the second fluid storage structure 22 is spaced from the first fluid storage structure 21 at least along a portion of the perimeter of the second fluid storage structure 22. Accordingly, in the exemplary embodiment shown in FIG. 5, the inner lateral walls 21c of the first fluid storage structure 21 are spaced from the lateral walls 22d of the second fluid storage structure 22. The spacing between the lateral walls 21c and 22d defines a pair of lateral gaps or channels 34 that permit the pad 10 to take-on a "cup" shape (FIG. 6) when worn, thus allowing the core 16 and the rest of the pad 10 to generally conform to the body 13 of the wearer. The "cup" shape (FIG. 6) attained by the core 16 facilitates the containment of bodily fluid secreted by the wearer and directs the body fluid trapped in the channels 34 to enter the first and second fluid storage structures 21, 22 through the lateral walls 21c, 22d. A contemplated variation of core 16 is illustrated in FIG. 7, in which like reference numerals refer to similar features in FIGS. 1-6. In that alternative embodiment, the core 16a shown in that figure has first and second fluid storage structures 21', 22', in which the second fluid storage structure 22' is spaced from the first fluid storage structure 21' along the entire periphery of the second fluid storage structure 22'. In that regard, the inner end walls 21f of the first fluid storage structure 21' are spaced from the respectively confronting end walls 22g of the second fluid storage structure 22'. The spacing between the end walls 21f and 22g define a pair of end gaps or channels 38, having functionality similar to that of the lateral channels 34 described above.

While FIGS. 5-7 depict embodiments in which both lateral walls 22d and/or both end walls 22g of the second fluid storage structure 22, 22' are spaced from the respectively confronting inner walls 21c, 21f of the first fluid storage structure 21, 21', other alternatives are contemplated that fall within the scope of the present disclosure. For example, and without limitation, only one of the lateral walls 22d and/or only one of the end walls 22g of the second fluid storage structure 22, 22' may be spaced from the corresponding confronting inner wall 21c or 21f of the first fluid storage structure 21, 21', while the other of the lateral walls 22d or of the end walls 22g may be substantially adjacent the respectively confronting inner wall 21c or 21f. Accordingly, while FIGS. 5-7 depict embodiments in which the channels 34, 38 define substantially symmetrical cores 16, 16a, it is contemplated that they may instead define asymmetrical cores, and still fall within the scope of the present disclosure.

Figure 8:
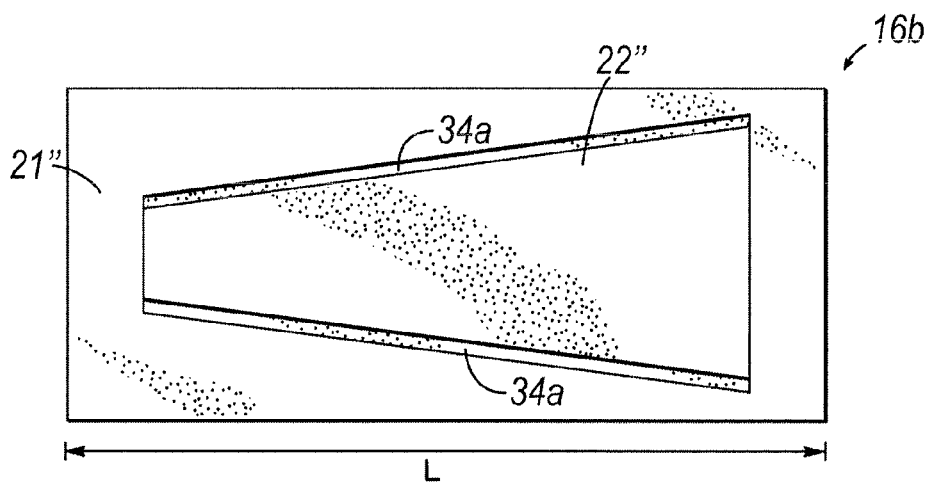
FIG. 8 is a top view, similar to FIGS. 5 and 7, illustrating a core in accordance with yet another embodiment of the invention.

In addition to the above, those of ordinary skill in the art will readily appreciate that the channels 34, 38 may or may not extend substantially along the length and width dimensions L, W, but be instead oriented so as to extend in any direction, depending on the shapes of the first and second fluid storage structures 21, 21' 22, 22'. FIG. 8 illustrates that type of contemplated alternative embodiment. In that embodiment, two lateral channels 34a are defined between first and second fluid storage structures 21" and 22" of the core 16b shown in that figure. The lateral channels 34a extend along directions that are transverse, rather than parallel, to the length dimension L of the core 16b.

Referring again to FIGS. 3 and 4, the respective thicknesses of the first and second fluid storage structures 21, 22 in those embodiments are substantially equal. In that regard, the top surfaces 21a, 22a of the first and second fluid storage structures 21, 22, adjacent the topsheet 12, are substantially coplanar i.e., the top surfaces 21a, 22a lie in planes that are spaced from one another by no more than about 5 mm. In those embodiments, accordingly, the resulting core 16 has a uniform thickness, which enhances the wearer's comfort and may be perceived as more aesthetically pleasing than cores having a non-uniform thickness. Further, this type of core has the advantages gained by having more than one (e.g., two) discrete fluid storage structures, without the need to increase the overall thickness of the core 16.

In one specific embodiment, the first fluid storage structure 21 has natural or synthetic fluff (e.g, cellulose fluff pulp), while the second fluid storage structure 22 is a generally rectangular structure (i.e., in a plane orthogonal to the thickness dimension t) made of a relatively rigid airlaid material which may or may not contain fluff pulp. In that embodiment, one or both of the fluid storage structures 21 and 22 may contain SAP or some other fluid-storage material. As used herein, the term "fluid storage structure" is intended to describe absorbent structures, forming part of the core of a disposable absorbent product, that substantially has a fluid storage function. In that regard, and without limitation, the fluid storage structures contemplated to fall within the scope of the present disclosure may contain natural or synthetic materials (e.g., SAP) that are predominantly configured to store, rather than to acquire or distribute fluid to other components that are intended to ultimately store the fluid secreted by the wearer. For example, fluid storage structures of the type contemplated herein may have a storage capacity in the range of about 60 grams to about 6000 grams, as measured by the Rothwell method (ISO 11948-1), known to those of ordinary skill in the art, and the description of which falls beyond the scope of the present disclosure.

Figure 9:
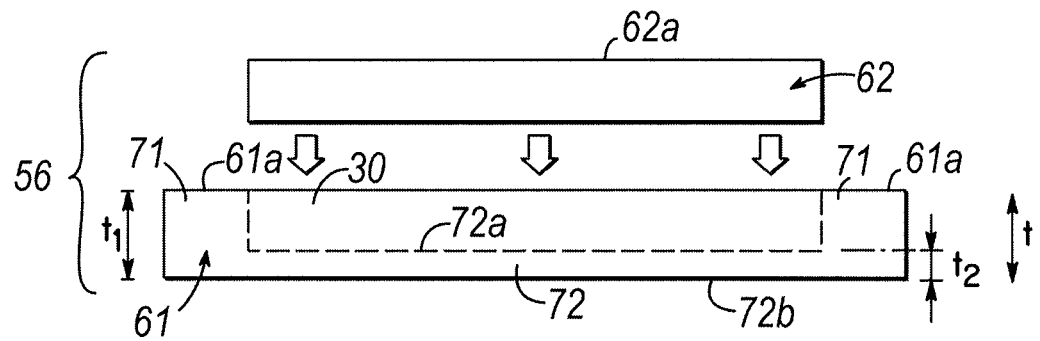
FIG. 9 is a partially disassembled view of a core in accordance with another embodiment of the invention.
Figure 10:
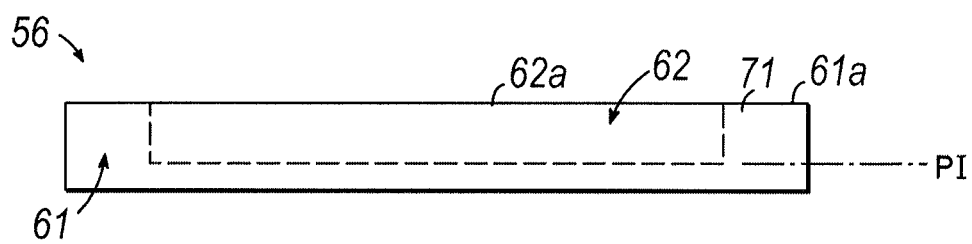
FIG. 10 is an assembled view of the core of FIG. 9.

Referring now to FIGS. 9 and 10, in which like reference numerals refer to similar features in the preceding figures, another embodiment of a core 56 is illustrated. Core 56 includes discrete first and second fluid storage structures 61, 62, with the first fluid storage structure 61 surrounding the second fluid storage structure 62 in the thickness dimension t. FIG. 9 illustrates a thickness difference in the first fluid storage structure 61, between an outer region 71 and a relatively thinner inner region 72. More specifically, the outer region 71 has a thickness $t_1$ that is greater than the thickness $t_2$ of the inner region 72. In that regard, the second fluid storage structure 62 rests within the shallower inner region 72, and is supported on a top surface 72a of the inner region 72. The top surface 72a of inner region 72 extends in a plane PI that is intermediate between the bottom surface 72b of the first fluid storage structure 61 and the top surface 61a of the outer region 71. The thicknesses $t_1$ and $t_2$ are suitably chosen such that, when the core 56 is assembled (FIG. 10), a top surface 62a of the second fluid storage structure 62 is substantially coplanar with the top surface 61a of the first fluid storage structure 61 at the outer region 71 i.e., the top surfaces 61a, 62a lie in planes that are spaced from one another by no more than about 5 mm. This configuration results in a core 56 having a uniform thickness, with advantages similar to those described with respect to the core 16 of the preceding figures.

Figure 11:
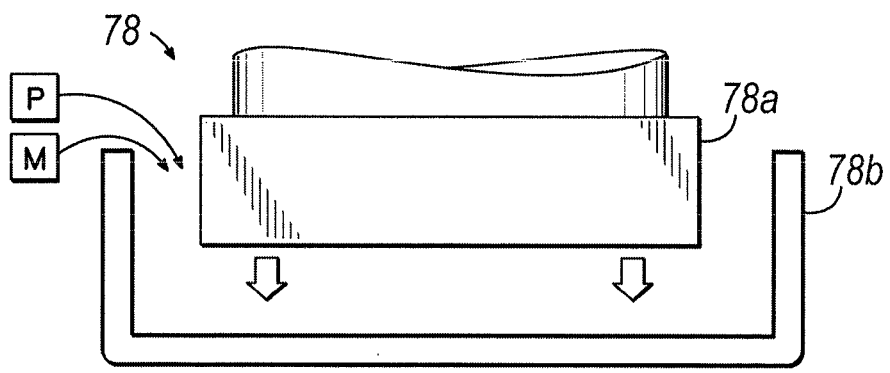
FIG. 11 is a schematic view of an apparatus for forming a portion of the core of FIGS. 9 and 10, in accordance with an embodiment of the invention.
Figure 11A:
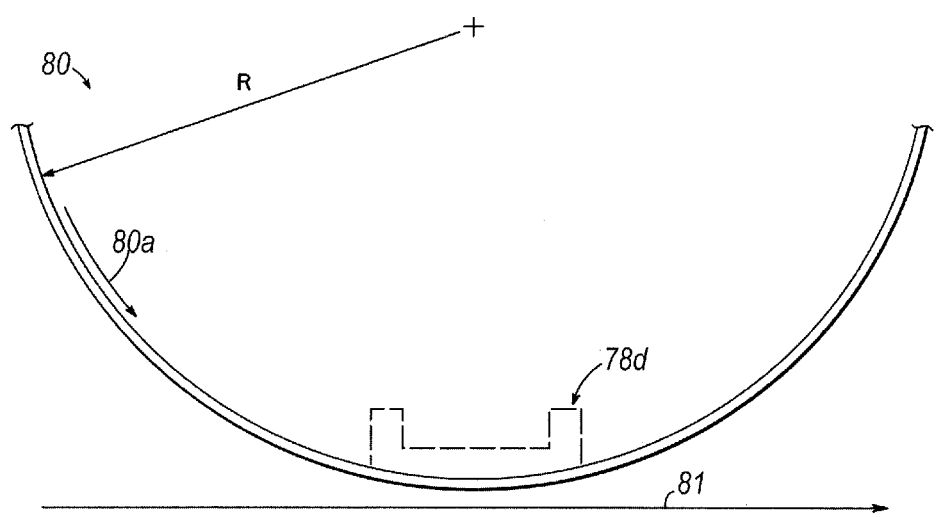
FIG. 11A is a schematic view of an apparatus for forming a portion of the core of FIGS. 9 and 10, in accordance with another embodiment of the invention.
Figure 12:
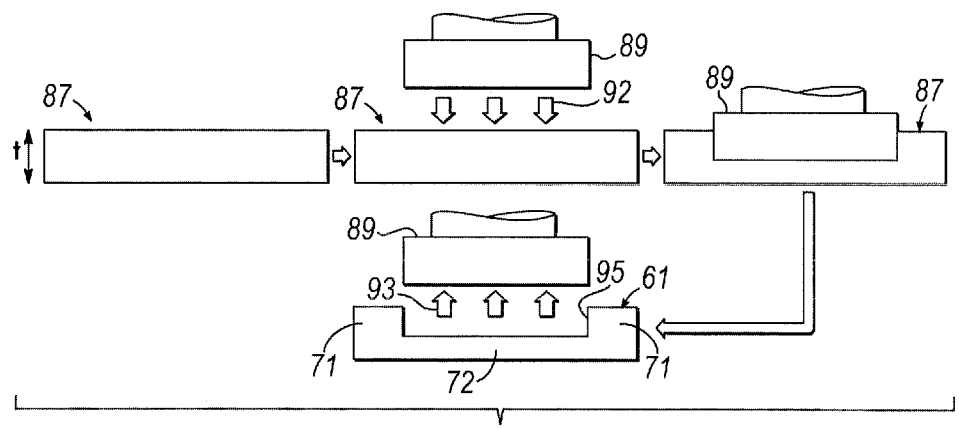
FIG. 12 is a schematic view of an apparatus and process for forming a portion of the core of FIGS. 9 and 10, in accordance with yet another embodiment of the invention.

With continued reference to FIGS. 9-10, and further referring to FIGS. 11, 11A, and 12, the gradient in thickness between the inner and outer regions 72, 71 of the first fluid storage structure 61 may be achieved by at least one of two contemplated methods. A first exemplary method, schematically illustrated in FIG. 11, includes forming the first fluid storage structure 61 (FIGS. 9-10) in a mold 78, by directing pulp P and/or other materials, as well as materials M primarily having a fluid storage function (e.g., SAP) into the mold 78. The mold 78 has the desired shape of the first fluid storage structure 61 to be formed. The mold 78 may be a single-component structure or instead may, as illustrated in FIG. 11, have a male mold component 78a and a female mold component 78b. The formed first fluid storage structure 61 may be then removed from the mold 78 and advanced to another stage of the process (not shown) to receive the second fluid storage structure 62 within the formed centrally located opening 30 of the first fluid storage structure 61.

Alternatively, the components making up the second fluid storage structure 62 may be added to the mold 78 so as to be received within the opening 30 on the top surface 72a. To that end, when using the exemplary two-component mold 78 illustrated in FIG. 11, this part of the process would entail moving the male and female components 78a, 78b away from one another so that the material(s) making up the second fluid storage structure 62 can be placed into the opening 30. The assembled structure i.e., the assembly made up of the first fluid storage structure 61 and the second fluid storage structure 62 may then be removed from the mold 78 and advanced to another stage of the pad manufacturing process.

FIG. 11A illustrates a variation of the process described above, in which a mold 78d forms part of a rotating drum 80, which may include one or more molds 78d (only one shown). Mold 78d has the desired shape of the first fluid storage structure 61 to be formed. The core-forming process thus entails directing pulp P and/or other materials, as well as materials M primarily having a fluid storage function (e.g., SAP) into the mold 78d and incorporating the material(s) making up the second fluid storage structure 62 in a subsequent step. The rotating drum 80 travels in a direction of rotation 80a, which places the contents of mold 78d onto moving conveyor vacuum belt 81 in a proportionately spaced configuration.

As described above, the second fluid storage structure 62 may be in the form of a relatively rigid layer of material (e.g., an airlaid-based material). A contemplated process for making the core 56 includes cutting a continuous web defining the rigid layer of material with a cut-and-slip apparatus and process and then placing the discrete cut piece of the rigid layer of material into the opening 30 (FIG. 9). The above-referenced continuous web may be made "in-line" i.e., as another part of the process for making the core 56, on the same manufacturing line as that for manufacturing the rest of the core 56. Alternatively, the above-referenced continuous web may be made off-line and supplied to the manufacturing line as a prefabricated web.

An exemplary cut-and-slip apparatus and process is described in U.S. Pat. No. 6,544,375, entitled "Process for Applying Discrete Web Portions to a Receiving Web," the contents of which are hereby expressly incorporated by reference herein. In this regard, embodiments of the invention in which the first fluid storage structure 61 is predominantly a relatively soft structure (e.g., made primarily from fluff pulp) and in which the second fluid storage structure 62 is a relatively rigid material, prevent exposure of the edges and/or corners of the second fluid storage structure 62. This, in turn, prevents or at least minimizes the likelihood of contact of those edges and/or corners with the wearer, which enhances the wearer's comfort. In addition, embodiments of this type facilitate the attainment of complex shapes (i.e., hourglass shape or some other regular or irregular shape) for the core 16, 56, while maintaining the simplicity in the processing of the relatively rigid second fluid storage structure 62. More specifically, embodiments are contemplated in which the first fluid storage structure 61 is a soft structure, made primarily of fluff pulp, and made, for example, in a drum mold having the desired regular or irregular shape of the storage structure 61. Further, in those embodiments, the relatively rigid material making up the second fluid storage structure 62 is cut into a simple shape e.g., a rectangular shape, using a simple process such as the cut-and-slip process discussed above. The end-result in those embodiments is a core 16, 56 having at least two fluid storage structures 61, 62, and also having the desired overall shape, absorption capacity, and high level of comfort for the wearer, without the drawbacks of conventional cores.

Yet another advantage of embodiments of the type described above, in which a relatively soft fluid storage structure surrounds a relatively rigid fluid storage structure, is the resulting enhanced fluid containment. More specifically, fluid is known to flow from an open, low density capillary structure, to a high density capillary structure, while it is known not to flow from a high density to a low-density capillary structure. In that regard, fluid received by the relatively high-density, rigid second fluid storage structure 62, will not have a tendency to flow outwardly, toward the relatively low-density, soft first fluid storage structure 61. Fluid received by the rigid second fluid storage structure 62, accordingly, will have a tendency to remain in that storage structure 62, which enhances the overall containment of fluid by the core 16, 56.

Whether the first fluid storage structure 61 and second fluid storage structure 62 are assembled together within a mold, or made at two different locations along the process, the assembled structure is then placed between a pair of confronting webs defining the topsheet 12 and backsheet 14 of the pad 10, for further disposition in the pad-manufacturing process. Prior to or subsequent to the placement of the assembled structure between the webs defining the topsheet 12 and backsheet 14, and while not shown, it is contemplated that the assembled structure may be calendered or passed through some other apparatus exerting an even amount of pressure over the first and second fluid storage structures 61, 62. Accordingly, in the embodiment illustrated at FIGS. 9 and 10, the core 56 therein may be made utilizing the method described above and result in a core in which the density of material (e.g., fluff pulp) in the outer region 71 is similar to that of the inner region 72.

While the process associated with FIG. 11 is described with reference to the core 56 of FIGS. 9 and 10, this is not intended to be limiting. Accordingly, it is contemplated that the principles discussed in connection with that process are similarly applicable to the formation of the core 16, 16a, or 16b of FIGS. 1-8.

FIG. 12 schematically illustrates another exemplary method for forming the core of pad 10. Specifically, that method may be used to form the first fluid storage structure 61 of the exemplary core 56 (FIGS. 9-10). That method includes forming the first fluid storage structure 61 so as to first obtain a partially-formed fluid storage structure 87 of generally uniform thickness. A schematically represented apparatus 89 (e.g., a calender roll) is then used to apply pressure (arrows 92) against a selected, central portion of the partially-formed fluid storage structure 87. That selected portion corresponds to the inner region 72 of the first fluid storage structure 61 (FIGS. 9-10). Movement of the apparatus 89 away from the first fluid storage structure 61 (arrows 93) leaves that structure 61 available to then receive the second fluid storage structure 62 (FIGS. 9-10) within a centrally located opening 95 formed in the first fluid storage structure 61. The localized pressure exerted by the apparatus 89 results in an inner region 72 that has a higher density of material (e.g., fluff pulp) than that of the outer region 71.

The exemplary apparatus and process described with reference to FIG. 12 contemplates leaving the outer region 71 of the first fluid storage structure 61 substantially uncompressed, with the pressure exerted by apparatus 89 being limited only to the portion corresponding to the inner region 72. A contemplated variant includes compressing both, the inner and outer regions of the partially-formed structure 87, but to different extents. More specifically, that alternative embodiment contemplates applying a first pressure to an outer region of the partially-formed structure 87, and a second pressure to an inner region of the partially-formed structure 87, with the second pressure being greater than the first pressure. Accordingly, in that embodiment, the inner region is compressed to a greater extent than the outer region, thereby resulting in the difference in thickness between the outer region 71 and inner region 72. The resulting density of fluff pulp for embodiments in which that type of material is substantially present in the first fluid storage structure 61, may be in the range from about 0.07 g/cm$^3$ to about 0.3 g/cm$^3$ in specific embodiments. Those of ordinary skill in the art will readily appreciate, however, that this range of densities is merely exemplary and thus not intended to be limiting.

Figure 13:
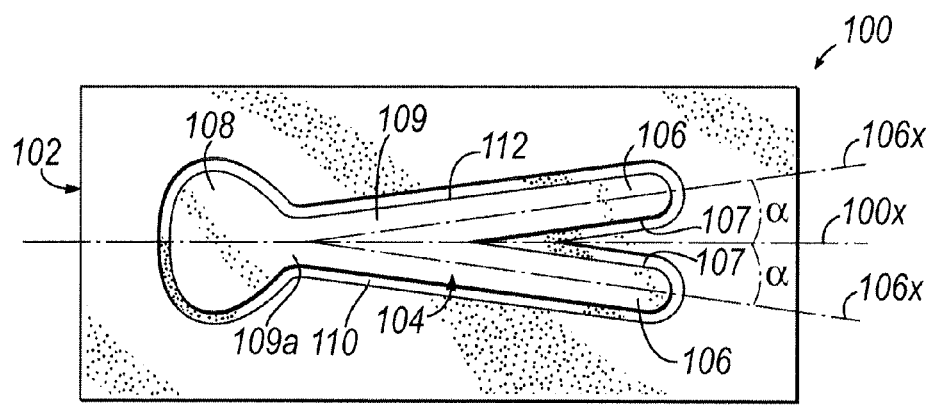
FIG. 13-17 are top views of cores of respective disposable absorbent products in accordance with various embodiments of the invention.
Figure 15:
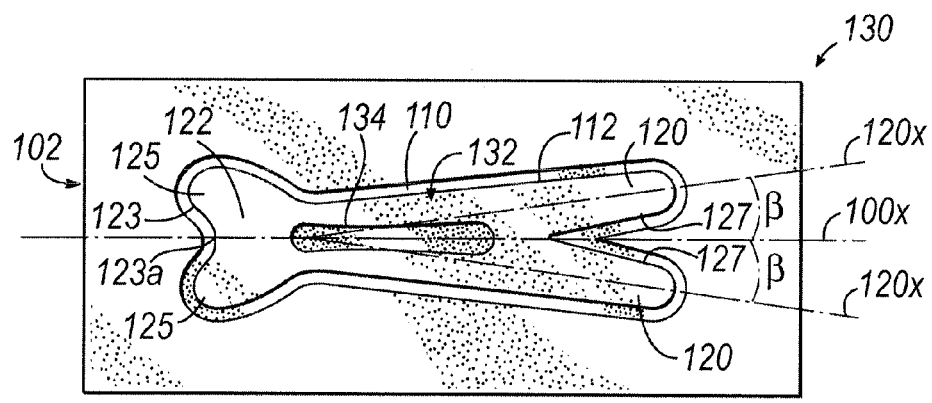
Figure 16:
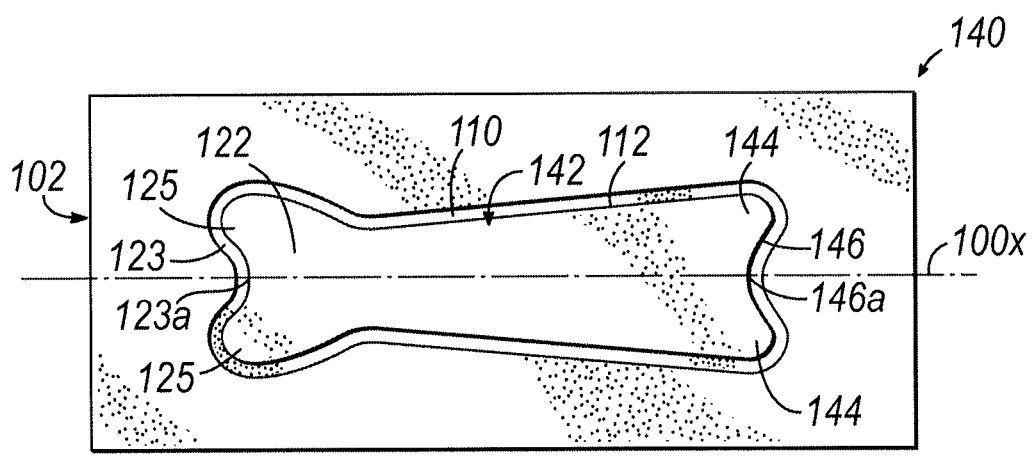
Figure 17:
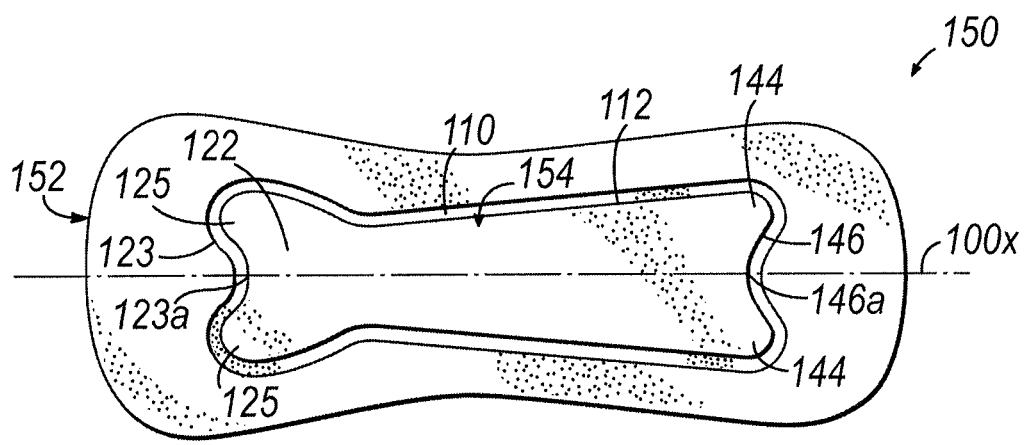

With reference to FIGS. 13-17, those figures illustrate exemplary cores according to various embodiments. It is contemplated that each of those embodiments may be made with the exemplary apparatus and according to the exemplary processes described with reference to FIGS. 9-11, 11A, and 12, above. For ease of understanding, like reference numerals throughout FIGS. 13-17 refer to features that are similar to one another. FIG. 13 illustrates an embodiment of a core 100 that includes a first fluid storage structure 102 surrounding a second fluid storage structure 104 in the thickness the mention, in a manner similar to those described above with respect to the first and second fluid storage structures in the embodiments of FIGS. 1-12. The description of the structural and functional relationships of the first and second fluid storage structures in FIGS. 1-12 may be referred to for an understanding of the structural and functional relationships of the embodiments of FIGS. 13-17 as well. In FIGS. 13-16, the first fluid storage structure 102 is illustrated as being generally rectangular, although this shape is intended to be exemplary rather than limiting, insofar as any regular or irregular shape is contemplated for first fluid storage structure 102 without deviating from the scope and spirit of the present disclosure. FIG. 17, for example, illustrates a variation in which the first fluid storage structure 152 therein has an hourglass shape.

Referring particularly to FIG. 13, the second fluid storage structure 104 extends longitudinally along an axis 100x. The second fluid storage structure 104 in the illustrated embodiment is shaped so as to include a pair of leg portions 106, each oriented at an acute angle from the axis 100x. More specifically, each of the leg portions 106 extends along a respective minor axis 106x, with each of the minor axes 106x defining an acute included angle α with the axis 100x. Included angle α is in some embodiments less than about 40°. In specific embodiments, angle α is less than about 20°. Further, in this embodiment, the included angle between the two minor axes 106x (i.e., the sum of the two adjacent angles α) is also acute and the respective inner walls 107 of the leg portions 106 are shaped so as to define a generally V-shaped profile between them. This particular geometry permits the two leg portions 106 to conform to the body of the wearer in use. The leg portions 106 jointly define one of the longitudinal ends of the second fluid storage structure 104. A head portion 108 also forms part of the exemplary second fluid storage structure 104, and is located at the opposite longitudinal end of second fluid storage structure 104. In the illustrated embodiment, the head portion 108 is generally oval in shape, although other regular or irregular shapes are contemplated. The head portion 108 in the embodiment of FIG. 13 is wider (i.e., the dimension orthogonal to the longitudinal axis 100x) than a central portion 109 of fluid storage structure 104, so as to define a neck 109a between the head portion 108 and central portion 109. The relatively large size of head portion 108 enhances absorption of fluids secreted by the wearer by virtue of being configured to lie against an area of the wearer's body that requires increased absorption.

With continued reference to FIG. 13, core 100 includes a gap 110 between the first and second fluid storage structures 102, 104, extending along the entire perimeter 112 of the second fluid storage structure 104. The gap 110 is similar, in structure and function, to the channels 34, 34a, and 38 of the embodiments of FIGS. 5-8, the description of which may be referred to for an understanding of the features of gap 110 as well. Alternative embodiments (not shown) are also contemplated in which the gap 110 extends along less than the entire perimeter 112 of fluid storage structure 104. Yet other embodiments are contemplated in which no gap is present at all between the first and second fluid storage structures 102, 104 i.e., in which the first and second fluid storage structures 102, 104 are in an abutting relationship with one another.

Figure 14:
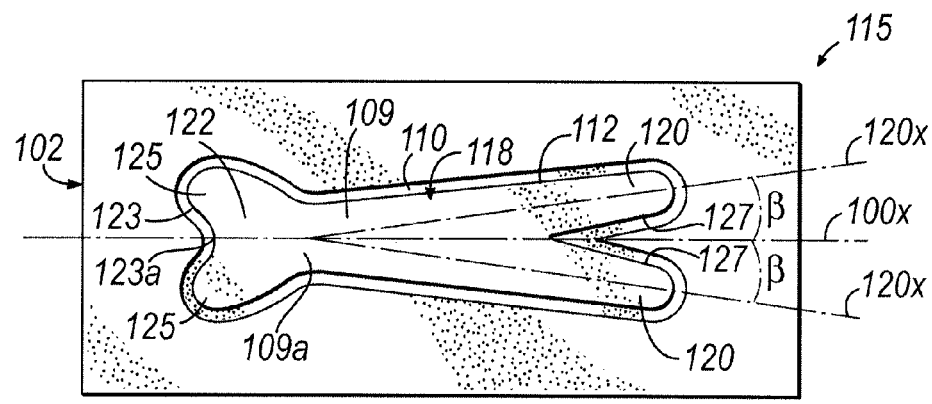

FIG. 14 illustrates a core 115, similar to core 100 of FIG. 13, in which the second fluid storage structure 118 has a pair of leg portions 120 shorter than those of the embodiment of FIG. 13. The second fluid storage structure 118 includes a head portion 122 having a contoured terminal surface 123, and a pair of arm portions 125 defining an arcuate depression 123a, on terminal surface 123, at the juncture between the arm portions 125. The shape of the arm portions 125, including that of the terminal surface 123, defines a generally heart-shaped head portion 122. This shape enhances the feminine appeal of the absorbent product of which core 115 forms part, thereby leading to increased satisfaction to the wearer. Head portion 122 is wider than a central portion 109 of fluid storage structure 118, so as to define a neck 109a between central portion 109 and head portion 122. The relatively large size of head portion 122 enhances absorption of fluids secreted by the wearer by virtue of being configured to lie against an area of the wearer's body that requires increased absorption.

In another aspect of the exemplary core 115, each of the leg portions 120 extends along a respective minor axis 120x, with each of the minor axes 120x defining an acute included angle β with the axis 100x. Further, in this embodiment, the included angle between the two minor axes 120x is also acute and the respective inwardly-facing walls 127 of the leg portions 120 are shaped so as to define a generally V-shaped profile at the juncture of leg portions 120. This particular geometry permits the two leg portions 120 to conform to the body of the wearer in use.

With particular reference to FIG. 15, the core 130 in that embodiment is similar in most respects to core 115 of FIG. 14. Core 130 includes a fluid storage structure 132 having a centrally located opening 134 that extends partially or totally through the thickness of fluid storage structure 132. In some embodiments, the void defined by central opening 134 enhances the rate of absorption of fluid secreted by the wearer. The opening 134 in the illustrated embodiment is an elongate opening, having a length between about 10% and about 80% of the overall length of the fluid storage structure 132. In specific embodiments, the opening 134 may have a length between about 30% and about 60% of the overall length of fluid storage structure 132. But those shapes and relative dimensions of opening 134 are not intended to be limiting, insofar as other shapes and relative dimensions are contemplated to be within the scope of the present disclosure.

FIG. 16 shows another embodiment of a core 140 similar to cores 115 and 130 (FIGS. 14 and 15). A fluid storage structure 142 of core 140 has leg portions 144 that are much shorter in length than those of the embodiments of FIGS. 13-15. Specifically, the length of each of leg portions 144 may be in the range of about 10% or less of the total length of the fluid storage structure 142. In specific embodiments, the length of leg portions 144 may be in the range of less than about 5% or less than about 3% of the total length of fluid storage structure 142. For sake of comparison, the leg portions 106 or 120 (FIGS. 13-15) may have a length in the range from about 20% to about 50% of the overall length of the respective fluid storage structure 104, 118, 132. As used herein, the "length" when referring to leg portions refers to the dimension of those leg portions measured in a direction parallel to the longitudinal axis 100x of the second fluid storage structure of which the leg portions form part. And the "length" of a fluid storage structure refers to the dimension of that fluid storage structure that extends between the terminal ends of that fluid storage structure, also measured in a direction parallel to the longitudinal axis 100x.

The leg portions 144 of the embodiment of FIG. 16 are arranged and shaped so as to define a contoured terminal surface 146 opposite the terminal surface 123 of head portion 125. The contoured terminal surface 146 includes an arcuate depression 146a providing a smooth transition at the junction between the leg portions 144. Depression 146a facilitates the movement of leg portions 144 to conform to the body of the wearer in use. The shape and length of the leg portions 144 may be preferred to those of the leg portions 106, 120 (FIGS.

13-15) insofar as they may be easier to manufacture when the fluid storage structure of which they form part is made of soft materials, such as fluff pulp.

Referring now to FIG. 17, the exemplary core 150 of that embodiment has first and second fluid storage structures 152, 154 similar to those of the preceding figures. In this embodiment, the second fluid storage structure 154 is similar to the second fluid storage structure 142 of core 140 (FIG. 16), but the first fluid storage structure 152 has an hourglass shape, rather than a generally rectangular shape. The soft contours of the exemplary hourglass-shaped first fluid storage structure 152 may be desirable to enhance the feminine appearance of the product of which core 150 forms part. Those of ordinary skill in the art will readily appreciate that other regular and irregular shapes are contemplated for either or both of the first and second fluid storage structures, all of which are considered to fall within the scope of the present disclosure.

While not shown, it is contemplated that the topsheet 12 (FIGS. 1 and 2) may have a print or embossed pattern following the shape of the first and/or second fluid storage structures of any of the embodiments of FIGS. 13-17, or the shape of any features of those fluid storage structures. This may be desirable to signal to the wearer of the product that a portion of the core is shaped in the form suggested by the print or embossed pattern on the topsheet 12. Additionally or alternatively, in embodiments having an embossed pattern, the embossing on the topsheet 12 may facilitate directing of fluid secreted by the wearer to specific portions of the core located under the topsheet 12. For example, and without limitation, a product may have an embossed pattern on the topsheet 12 that directs fluid toward an opening such as the exemplary central opening 134 in the embodiment of FIG. 15, or toward an open area such as gap 110 (FIGS. 13-17), if present.

Referring generally to the different embodiments illustrated in the preceding figures, the thicknesses of the first fluid storage structure 21, 21', 21", 61, 102 and of the second fluid storage structure 22, 22', 22", 62, 104, 118, 132, 142, 154 are suitably chosen, as are the basis weights of materials making up those two fluid storage structures. For example, and without limitation, the first fluid storage structure 21, 21', 21", 61, 102 may include fluff pulp in a basis weight in the range from about 200 g/m² to about 1000 g/m² and, more particularly, in the range from about 200 g/m2 to about 600 g/m2. In addition or alternatively, the first fluid storage structure 21, 21', 21", 61, 102 may include SAP in a basis weight in the range from about 0 g/m² to about 600 g/m². The thickness of the first fluid storage structure 21, 21', 21", 61, 102 may be in the range from about 0.5 mm to about 12 mm. In another non-limiting example, the second fluid storage structure 22, 22', 22", 62, 104, 118, 132, 142, 154 may be made of an airlaid material and/or contain SAP. The airlaid material in that example may be present in a basis weight in the range from about 80 g/m² to about 1000 g/m², for example, while the SAP may be present in a weight-percentage in the range from about 5% to about 80% and, more particularly, in the range from about 5% to about 60%. In that example, moreover, the thickness of the second fluid storage structure 22, 22', 22", 62, 104, 118, 132, 142, 154 may be in the range from about 0.5 mm to about 12 mm, for example. Exemplary airlaid materials suitable as the second fluid storage structure 22, 22', 22", 62, 104, 118, 132, 142, 154 are materials known under the names "Airlaid 460 g/m², 45% SAP, Multibonded, 4.0 mm;" "w76, 460 g/m², multibond material, fw1200;" and "w86, 600 g/m², multibond material, fw1000," "VH460.103.B6001;" and "VH600.101.B6001," all commercially available from Glatfelter Falkenhagen GmbH, of Falkenhagen, Germany. In yet another example, the second fluid storage structure 22, 22', 22", 62, 104, 118, 132, 142, 154 may be a foam-based material that may or may not contain SAP. Example of suitable foam-based materials are High Internal Phase Emulsion (HIPE) foams, such as those described in U.S. Pat. Nos. 5,387,207; 5,260,345; 5,650,222; and 5,849,805, the respective disclosures of which are hereby expressly incorporated by reference herein in their entirety.

Those of ordinary skill in the art will readily appreciate that, while the embodiments illustrated and described herein refer to a feminine pad, they are similarly applicable to other types of disposable absorbent products. For example, and without limitation, the principles and structures described herein are similarly applicable to baby diapers, adult diapers, incontinence guards, pantiliners, and other products in which absorbent structures are required for containment and absorption of fluids secreted by a wearer. Similarly, it is contemplated that the structures described herein can be used to manufacture only absorbent cores, rather than full disposable absorbent products. More specifically, embodiments are contemplated consisting of a core insert manufactured in one location and which is then supplied to another manufacturing location or to a consumer, to be used with a disposable absorbent product or even with a non-disposable absorbent product (e.g., underwear or brief).

From the above disclosure of the general principles of the present invention and the preceding detailed description of exemplary embodiments, those skilled in the art will readily comprehend the various modifications to which this invention is susceptible. Accordingly, this invention is intended to be limited only by the scope of the following claims and equivalents thereof.

What is claimed is:

1. A disposable absorbent product comprising:
a backsheet;
a topsheet overlaying said backsheet; and
a core disposed between said backsheet and said topsheet for retaining fluid secreted by a wearer of the absorbent product, said core including first and second fluid storage structures, each having a respective length dimension, a respective width dimension, and a respective thickness dimension orthogonal to said respective length and width dimensions,
wherein:
said respective thickness dimensions of said first and second fluid storage structures overlap one another,
said second fluid storage structure extends along a longitudinal axis,
said second fluid storage structure has a head portion and a pair of leg portions longitudinally opposed said head portion, and
each of said leg portions extends along a minor axis defining an acute included angle with said longitudinal axis.

2. The disposable absorbent product of claim 1, wherein said leg portions are oriented so as to define an acute included angle between said minor axes.

3. The disposable absorbent product of claim 1, wherein said included angle is less than about 40°.

4. The disposable absorbent product of claim 3, wherein said included angle is less than about 20°.

5. The disposable absorbent product of claim 1, wherein the length of each leg portion is less than 10% of the overall length of said second fluid storage structure.

6. The disposable absorbent product of claim 1, wherein the length of each leg portion is greater than 20% of the overall length of said second fluid storage structure.

7. The disposable absorbent product of claim 1, wherein each of said leg portions has an inwardly-facing wall, said inwardly-facing walls defining a generally V-shape juncture between said leg portions.

8. The disposable absorbent product of claim 1, wherein said second fluid storage structure includes an arcuate depression defining a juncture between said leg portions.

9. The disposable absorbent product of claim 1, wherein said second fluid storage structure includes a central portion between said head portion and said leg portions, said head portion being wider than said central portion.

10. The disposable absorbent product of claim 1, wherein said head portion has a generally oval shape.

11. The disposable absorbent product of claim 1, wherein said head portion has the general shape of a heart.

12. The disposable absorbent product of claim 1, wherein said head portion includes a pair of arm portions and an arcuate depression defining a juncture there between.

13. The disposable absorbent product of claim 1, wherein said second fluid storage structure has a centrally-located opening extending through the thickness thereof.

14. The disposable absorbent product of claim 1, wherein said first fluid storage structure has an hourglass shape.

15. A disposable absorbent product comprising:
a backsheet;
a topsheet overlaying said backsheet; and
a core disposed between said backsheet and said topsheet for retaining fluid secreted by a wearer of the absorbent product, said core including first and second fluid storage structures, each having a respective length dimension, a respective width dimension, and a respective thickness dimension orthogonal to said respective length and width dimensions,
wherein:
said respective thickness dimensions of said first and second fluid storage structures overlap one another,
said second fluid storage structure has a head portion and a pair of leg portions longitudinally opposed said head portion,
each of said leg portions extends along a minor axis defining an included angle of less than 40° there between, and
each of said leg portions has a length greater than 20% of the overall length of said second fluid storage structure.

16. The disposable absorbent product of claim 15, wherein said head portion is generally oval-shaped.

17. The disposable absorbent product of claim 15, wherein said head portion is generally heart-shaped.

18. The disposable absorbent product of claim 15, wherein said second fluid storage structure includes a centrally located, elongate opening extending through the thickness thereof.

19. The disposable absorbent product of claim 15, wherein said first and second fluid storage structures are spaced from one another along at least a portion of the periphery of said second fluid storage structure.

20. A disposable absorbent product comprising:
a backsheet;
a topsheet overlaying said backsheet; and
a core disposed between said backsheet and said topsheet for retaining fluid secreted by a wearer of the absorbent product, said core having a length dimension, a width dimension, and a thickness dimension orthogonal to the length and width dimensions, said core including first and second fluid storage structures, said first fluid storage structure at least partially surrounding said second fluid storage structure in the thickness dimension,
wherein:
said second fluid storage structure has a generally heart-shaped head portion and a pair of leg portions longitudinally opposed said head portion,
each of said leg portions has a length less than 10% of the overall length of said second fluid storage structure, and
said second fluid storage structure includes an arcuate depression defining a juncture between said leg portions.

21. An absorbent core for use in an absorbent product, the absorbent core comprising:
a first fluid storage structure; and
a second fluid storage structure,
wherein
said first and second fluid storage structures have respective length, width, and thickness dimensions, each said thickness dimension being orthogonal to said respective length and width dimensions,
said respective thickness dimensions of said first and second fluid storage structures overlap one another,
said second fluid storage structure extends along a longitudinal axis, and includes a head portion and a pair of leg portions longitudinally opposed said head portion, and
each of said leg portions extends along a minor axis defining an acute included angle with said longitudinal axis.

* * * * *